United States Patent [19]

Desai et al.

[11] Patent Number: 4,768,653
[45] Date of Patent: Sep. 6, 1988

[54] URINE SPECIMEN MAINTENANCE FORMULA

[75] Inventors: Jayraj S. Desai, Closter; Jack J. Mehl, Landing, both of N.J.

[73] Assignee: Becton, Dickinson and Company, Franklin Lakes, N.J.

[21] Appl. No.: 139,224

[22] Filed: Dec. 29, 1987

Related U.S. Application Data

[60] Division of Ser. No. 437,411, Oct. 28, 1982, Pat. No. 4,726,950, which is a continuation-in-part of Ser. No. 378,586, May 17, 1982, abandoned.

[51] Int. Cl.$^4$ .................. A01N 59/14; B65D 81/20
[52] U.S. Cl. .................. 206/569; 206/524.8; 424/148
[58] Field of Search .................. 206/524.8, 569; 424/148

[56] References Cited

U.S. PATENT DOCUMENTS 4,258,032 3/1981 Mehl .................. 424/148

OTHER PUBLICATIONS

Windholz (Editor) *The Merck Index*, (Merck & Co., Inc., Rahway, NJ) 9th Edition, p. 985 (1976).

Hayashi et al., *Chemical Abstracts*, vol. 79, 143511j (1973), p. 80.
Carrero, *Chemical Abstracts*, 1951, vol. 45, 6110h.
Ploquin et al., *Chemical Abstracts*, vol. 57, 10352 (1967).
Mehta, *Chemical Abstracts–Tenth Collective Index*–vols. 86–95, 1977–1981–*Chemical Substances Aluminocalcium–Azamina 8001RD* (American Chemical Society, 1979) pp. 3054C8 and 90: p. 36114n (1978).

*Primary Examiner*—Jimmy G. Foster
*Attorney, Agent, or Firm*—Robert P. Grindle

[57] ABSTRACT

A urine specimen maintenance formulation is provided which, when the urine specimen is added, maintains the specimen in the desired unaltered form for subsequent testing, without the need for refrigeration or other preservation measures, while simultaneously preventing any additional bacterial growth in the specimen. The formula of the invention includes distilled water, mannitol, boric acid and sodium borate. Additionally, the formula may include a buffer, such as sodium acetate, glutamine or other amino acids, and a surface active or dispersing agent to facilitate concentration of cellular elements during subsequent centrifugation of the sample for microscopic examination, as well as to facilitate preservation of organisms.

7 Claims, 1 Drawing Sheet

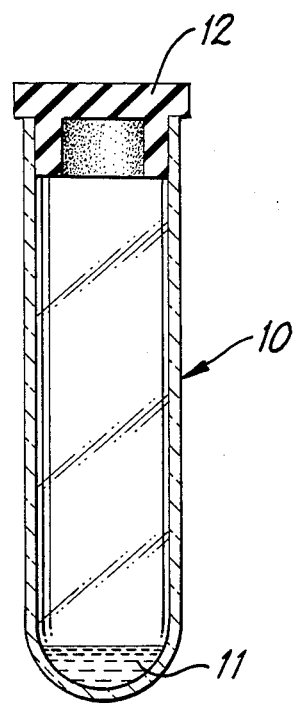

URINE SPECIMEN MAINTENANCE FORMULA

This is a division, of application Ser. No. 437,411, filed 10/28/82, now U.S. Pat. No. 4,726,950, which is a continuation-in-part of Ser. No. 378,586 filed May 17, 1982.

BACKGROUND AND STATEMENT OF THE INVENTION

Generally speaking, this invention relates to a liquid formulation for maintaining urine specimens. More particularly, this invention relates to such a formulation wherein urine specimens are maintained from the addition of the specimen until such time as testing of the specimen takes place, without any other preservation methods such as refrigeration, and which formulation simultaneously prevents additional growth of bacteria present in the specimen so that a precise accurate specimen is presented for examination. This invention is related to the inventions described and claimed in U.S. patent application Ser. No. 3,237 filed Jan. 15, 1979, now U.S. Pat. No. 4,258,032, issued Mar. 24, 1981, and U.S. application Ser. No. 209,816 filed Nov. 24, 1980 now U.S. Pat. No. 4,336,880, issued June 29, 1982, both of which applications are hereby incorporated by reference in their entirety.

Bacterial quantitation of clean-voided urine specimens is employed to determine the presence of urinary tract infection. In many cases, however, such specimens are contaminated from exogenous sources. Also, in view of the fact that urine has the capability of supporting the proliferation of bacteria, multiplication of such contaminants may occur which will result in false positives. As a result, in order to prevent multiplication of contaminants, it has been recommended in the past that culturing take place of a urine specimen within two to four hours of the taking of the specimen, or that refrigeration be applied to the specimen. As will be appreciated, in many cases such culturing or refrigeration is not possible. Therefore, there is a need for a maintenance formula for urine specimens which is capable of maintaining and preserving the urine intact once the sample is taken, and until such time as the sample may be examined, and which maintenance formula prevents multiplication of bacterial contaminants. In the past, powdered boric acid has been proposed as a preservative. However, boric acid is toxic to test strains present in urine. Therefore, the addition of boric acid will provide inaccurate results in some cases. Moreover, such powdered boric acid is not effective for preventing proliferation of some bacterial contaminant strains.

By contrast, in accordance with the present invention, there is provided a liquid maintenance formula for urine specimens comprising distilled water, sorbitol, boric acid, or salts thereof, and an alkali formate. The components of the formula are maintained in the formula in an amount effective to maintain a urine specimen in its initial form. It has been found with the formula of the invention that a urine sample is maintained without proliferation of bacterial contaminants, and simultaneously, is not unduly toxic to the bacteria present in the specimen.

A modified formulation, also found to be effective in manufacturing urine specimens for transporting them over a period of time without refrigeration, includes mannitol, sodium borate, and boric acid in distilled water. This particular formulation has proved to be particularly effective for status quo maintenance of microbial systems containing *streptococcus faecalis*. Also, it will preserve urine specimens containing *pseudomonas aeruginosa* at ambient temperatures for up to 72 hours.

While the urine maintenance formulation described and claimed in the above noted applications has proved effective for maintaining urine specimens without refrigeration, the formulation has certain disadvantages in that the formulation cannot be lyophilized for certain applications. Moreover, the viscosity thereof may provide difficulties in handling in certain applications. Also, those formulations containing glycerin are light sensitive over a period of time. In addition, the formulation may not be sterilized by irradiation.

By contrast, the sorbitol formulation herein is a solution with a reduced viscosity providing a liquid which is more easily dispensed, and providing a more accurate volume control during dispensing. Moreover, it allows freeze drying of the solution, thus eliminating dilution of the urine, and providing a product which may be sterilized by irradiation.

Indeed, the modified formulation containing mannitol discussed above may be lyophilized rapidly as compared to the formulation containing sorbitol. Also, the stability of the formulations are increased and their light sensitive properties are reduced substantially. A further important advantage of the formulations are that the specific gravity of the urine remains within diagnostic tolerances when the sample is added to the maintenance fluid. For example, the formulations consistently raise the specific gravity only 0.006, whereas a glycerin containing formulation raises the specific gravity beyond readable limits in certain applications with a urine refractometer.

In considering generally the conditions for achieving the most enhanced results in connection herewith, which conditions are more specifically set forth below, one may note that satisfactory results have been achieved in accordance herewith with a sorbitol formulation containing distilled water within the range of between about 85 and 105 ml. and preferably 100 ml., sorbitol within the range of between about 15 and 25 gms., and prefereably 20 gms., boric acid or salts thereof, such as sodium borate within the range of between about 8 and 12 gms., and preferably 10 gms., and an alkali formate within the range of between about 4 and 6 gms. and preferably 5 gms. The alkali formate may be, for example, sodium formate.

The formulations may include as an additional component, a buffer. A representative buffer is sodium acetate for example, which may be present within the formulation within the range of between about 4 and 6 gms. and preferably 5 gms. Other buffers may be used such as organic buffers including tris hydroxymethyl amino methane. Also, inorganic phosphate buffers may be used.

Glutamine or other amino acids such as arginine may be included specifically for the purpose of facilitating maintenance of the Pseudomonas species. The glutamine or other amino acid may be present within the range of between about 0.15 and 0.25 gms. and preferably 0.20 gms.

Also, a surfactant such as a non-ionic polysorbate 80 USP, present in the amount within the range of between about 0.5 and 0.7 ml, and preferably 0.6 ml may be included in the formulations. Such a representative non-ionic surfactant may be, for example, a one percent solution of Tween 80, a polyoxyethylene sorbitan monoleate, a product of Atlas Corporation. Other surfactants may be, for example, amphoteric compounds containing carboxylate or phosphate groups such as, for example, proteins or polypeptides, lecithins or cephalins, or other non-ionic compounds such as fatty acid esters, propylene glycol, sorbitan, or sucrose.

With the mannitol containing formulation, satisfactory results are achieved with a formulation containing distilled water within the range of between about 85 and 115 ml., and preferably 100 ml., mannitol within the range of between about 9 and 11 grams, and preferably 10 grams, boric acid within the range of between about 4.5 and 5.5 grams, and preferably 5 grams, and sodium borate within the range of between about 10.8 and 13.2 grams, and preferably 12 grams.

One of the aspects of this invention to be considered in the context of the maintenance of a urine sample is that it is desirable, in accordance with this invention, to have a final percentage of the active components of the sorbitol maintenance formulation herein present in specific amounts in the sample once the addition of the urine sample is made. For example, preferably, sorbitol is present within the range of between about 1.5 and 2.5 percent in the combined urine and maintenance formula, boric acid is present within the range of between about 0.8 and 1.2 percent, and sodium formate is present within the range of between about 0.4 and 0.6 percent. If glutamine is used additionally, it will be present within the range of between about 0.015 and 0.025 percent. By the same token, if a surfactant is used such as for example, Tween 80, which is a one percent solution, the final percentage quantity present in the combined urine maintenance formula sample will be within the range of 0.0005 and 0.0007 percent. If a buffer is used such as sodium acetate, for example, it will be present within the range of between about 0.4 and 0.6 percent.

If, on the other hand, the mannitol containing formulation is used the various components should be present in a urine sample, as follows: assuming a 5 ml. sample of urine, then mannitol should be present in the same within the range of between about 0.9 and 1.1 percent of the urine sample; sodium borate should be present in the amount within the range of between about 1.08 and 1.32 percent, and boric acid should be present in the amount within the range of between about 0.45 and 0.55 percent.

As will be appreciated, a lesser quantity of components is required for the mannitol urine specimen maintenance formula in accordance with this invention, thus making it simpler and less expensive for formulate.

As purely illustrative of the results achieved by the maintenance formulas, in accordance herewith, examples were prepared using the preferred ratio of components in the sorbitol containing maintenance formula. It is to be understood, that these examples are being presented with the understanding that they are to have no limiting character on the broad disclosure of the invention as generally set forth herein and as directed to men skilled in the art.

EXAMPLES

Twenty-four (24) hour cultures of two strains of *E. coli, C. freundii, P. mirabilis, S. faecalis* and *P. aeruginosa* in urine were used as primary inocula.

To each sterile plastic cup containing 40 ml. of filter sterilized urine pool (collected from two (2) healthy males), 0.01 ml. of urine culture was inoculated with auto-pipette with sterile plastic tip. The contents were mixed thoroughly before transferring in 5 ml. volumes into maintenance fluid tubes. 0.001 ml. from each of inoculated urines and preserved urines was delivered on blood agar plates (10% horse blood in Trypitcase Soy agar) and streaked with sterile glass angular spreader. The plates were incubated for 24 hours at 37° C. At the end of incubation period, plates were observed for colonial growth. The colonies were counted and after averaging (duplicate count), the derived number was multiplied by 1,000 to get Colony Forming Units (CFU) per milliliter of urine or preserved urine. The CFU per ml. was further converted into logarithmic expression to read $Log_{10}$ CFU/ml. The counts were done after 24 hours and 48 hours. During this period, the urines were maintained at 4° C. in the refrigerator while the urines in maintenance fluids were kept in incubator maintained at 28° C. The $Log_{10}$ CFU/ml. within 0.5 log between zero count and 48 hours count was considered adequate.

The Table below shows the maintenance patterns of the microorganisms wherein Lot A is a maintenance formulation containing sorbitol according to the invention herein with each tube containing 0.4 ml. solution which has been lyophilized, and sterilizer by $CO^{60}$ radiation at 2.0 Megarads; Lot B is the same as Lot A, but in a liquid form, and sterilized at 1.5 Megarads; Lot C is a boroglyceric acid formulation with sodium hydroxide which has been sterilized by $CO^{60}$ at 2.18 Megarads; and Lot D is the same as Lot C, but not sterilized by $CO^{60}$ irradiation.

TABLE

|  | Hours | E. coli (1) | E. coli (2) | C. freundii | P. mirabilis | S. faecalis St. Agnes strain | P. aeruginosa |
|---|---|---|---|---|---|---|---|
| Urine (4° C.) | 0 | 23,000 (4.36) | 62,000 (4.79) | 81,000 (4.91) | 65,000 (4.81) | 72,000 (4.86) | 72,000 (4.86) |
|  | 24 | 17,000 (4.23) | 68,000 (4.83) | 76,000 (4.88) | 80,000 (4.90) | 60,000 (4.79) | 65,000 (4.81) |
|  | 48 | 21,000 (4.32) | 77,000 (4.88) | 66,000 (4.82) | 86,000 (4.93) | 62,000 (4.79) | 62,000 (4.79) |
| Lot A | 0 | 25,000 (4.39) | 71,000 (4.85) | 91,000 (4.95) | 72,000 (4.85) | 77,000 (4.88) | 63,000 (4.79) |
|  | 24 | 31,000 (4.49) | 76,000 (4.89) | 116,000 (5.06) | 87,000 (4.94) | 91,000 (4.96) | 64,000 (4.80) |
|  | 48 | 41,000 (4.61) | 97,000 (4.98) | 129,000 (5.11) | 97,000 (4.98) | 131,000 (5.12) | 61,000 (4.78) |
| Lot B | 0 | 9,000 (3.95) | 63,000 (4.79) | 48,000 4.83 | 66,000 (4.82) | 68,000 (4.83) | 54,000 (4.75) |
|  | 24 | 11,000 (4.04) | 53,000 (4.72) | 42,000 (4.62) | 44,000 (4.64) | 42,000 (4.62) | 55,000 (4.74) |

TABLE-continued

|  | Hours | E. coli (1) | E. coli (2) | C. freundii | P. mirabilis | S. faecalis St. Agnes strain | P. aeruginosa |
|---|---|---|---|---|---|---|---|
|  | 48 | 14,000 (4.14) | 53,000 (4.72) | 44,000 (4.64) | 44,000 (4.64) | 45,000 (4.65) | 49,000 (4.69) |
| Lot C | 0 | 11,000 (4.04) | 59,000 (4.77) | 61,000 (4.78) | 61,000 (4.78) | 63,000 (4.79) | 59,000 (4.77) |
|  | 24 | 14,000 (4.14) | 24,000 (4.38) | 0 × 10 (−) | 15,000 (4.17) | 25,000 (4.39) | 16,000 (4.20) |
|  | 48 | 6,000 (3.77) | 4,000 (3.60) | 0 × 10 (−) | 6,000 (3.79) | 12,000 (4.08) | 100 (2.0) |
| Lot D | 0 | 19,000 (4.28) | 51,000 (4.70) | 73,000 (4.86) | 59,000 (4.77) | 62,000 (4.79) | 52,000 (4.72) |
|  | 24 | 11,000 (4.04) | 36,000 (4.55) | 44,000 (4.64) | 61,000 (4.78) | 59,000 (4.77) | 29,000 (4.46) |
|  | 48 | 14,000 (4.14) | 33,000 (4.52) | 40,000 (4.60) | 56,000 (4.75) | 63,000 (4.79) | 22,000 (4.34) |

As can be seen in the Table above, the results show that $CO^{60}$ sterilized sorbitol based formulae Lot A and Lot B performed satisfactorily in maintaining microbial populations in status quo number for 48 hours at 28° C., regardless of lyophilized or liquid form, and was comparable with refrigerated urine control. In contrast the $CO^{60}$ sterilized (2.18 MRADS) boroglyceric formula Lot C showed inhibition of *Citrobacter freundii* in 24 hours at 28° C. There was log reduction in number of *Escherichia coli* 2, *Proteius mirabilis* and *Pseudomonas aeruginosa* in 48 hours at 28° C. On the other hand, non-irradiated boroglyceric showed status quo maintenance of microbial populations for 48 hours at 28° C., as expected.

The data show that the sorbitol based formulation of the invention has the advantage over a boroglyceric acid formulation, in that the sorbitol based formula can be lyophilized, whereas a boroglyceric acid formulation cannot be lyophilized; and the sorbitol base maintenance fluid in either form can be sterilized by gamma radiation ($CO^{60}$) without affecting efficacy, whereas glyceroboric formula cannot be gamma irradiated without causing damage to the formulation for adequately maintaining the status quo number of microorganisms.

The present invention is particularly advantageous, as discussed above, in that it has been found that by employing the the maintenance formulas of the present invention for maintaining urine samples, the urine maintenance is favorably comparable to that obtained by refrigeration. As a result, by proceeding in accordance with the present invention, it is not necessary to effect refrigeration of a urine sample. Moreover, the present invention offers the advantage that urine maintenance can be effected with small amounts of the maintenance formula, thereby eliminating the necessity of employing a dilution factor in the sample determination.

The sorbitol maintenance formula of the present invention may be introduced into an evacuated container, in the amount of 0.5 ml. of the maintenance formula of the invention comprised from a solution prepared of 100 ml. of distilled water, 20 gms. sorbitol, 10 gms. boric acid, and 5 gms. sodium formate. The formulation making up the 0.5 ml. quantity to be added to the evacuated container may contain, in addition a buffer of 5 gms. of sodium acetate, glutamine in the amount of 0.2 gms. and Tween 80 in the amount of 0.6 ml.

Both the maintenance sorbitol and the mannitol containing formulas as discussed above, are preferably formulated to provide the range of percentages of the various active components, as discussed above, present in the evacuated container in the urine sample introduced therein.

With the foregoing and additional objects in view, this invention will now be described in further detail, and other objects and advantages thereof will be apparent from the following description, the accompanying drawing, and the appended claims.

DETAILED DESCRIPTION OF THE DRAWING

The single FIGURE shows a vertical sectional view of an evacuated container, illustrating the use of the urine maintenance formula of the invention.

As shown in the drawing, there is provided an evacuated tube 10 closed by stopper 12, which includes a maintenance formula 11 in accordance with the invention. The maintenance formula 11 is included in an amount to preserve the sample quantity which will be drawn into the tube upon piercing the stopper 12. A urine sample can be transferred to tube 10 as known in the art by piercing stopper 12 with a cannula. A sample cup for facilitating such introduction is disclosed in U.S. application Ser. No. 859,591 filed Dec. 12, 1977, now U.S. Pat. No. 4,116,006.

Accordingly, and as will be apparent from the foregoing, there are provided, in accordance herewith, maintenance formulas for preserving urine samples and maintaining the character thereof from the time of the taking of the sample until such time as the sample can be examined. The maintenance formulas have a reduced viscosity providing a liquid which is more easily dispensed, and which provides a more accurate volume control during dispensing. In addition, the maintenance formulas herein allow freeze drying, if desired, or the maintenance formula may be maintained in liquid form. Moreover, they may be sterilized by irradiation, and the stability thereof is maintained in the presence of exposure to light over a long period. Also the specific gravity or urine introduced into the maintenance formulas herein remains within diagnostic tolerances when the sample is added so that the sample is within readable limits with a urine refractometer.

In the event that *streptococcus faecalis* or a *pseudomonas* species is involved the mannitol containing formulation herein is especially effective. Moreover, it is particularly appropriate for mass production procedures, because of the reduced number of components making up the formulation.

While the compositions herein disclosed form preferred embodiments of this invention, this invention is not limited to those specific compositions, and changes can be made therein without departing from the scope of the invention which is defined in the appended claims.

What is claimed is:

1. A device for maintaining urine specimens, comprising
   (a) an evacuated specimen container;
   (b) a liquid composition for the bacteriostatic maintenance of urine specimens in said container;
   (c) said liquid composition comprising
      (1) boric acid;
      (2) sodium borate;
      (3) water; and
      (4) mannitol;
   (d) said boric acid, said sodium borate, said water and said mannitol being present in amounts effective for providing a maintenance composition for a urine sample; and
   (e) said boric acid, said sodium borate and said mannitol being dissolved in said composition to provide within the range of between about 0.45 and 0.55 percent boric acid, within the range of between about 1.08 and 1.32 percent sodium borate, and within the range of between about 0.9 and 1.1 percent mannitol in a urine sample introduced into said device.

2. The device of claim 1, further characterized by
   (a) said boric acid being present within the range of between about 4.5 and 5.5 grams;
   (b) said sodium borate being present within the range of between about 10.8 and 13.2 grams;
   (c) said mannitol being present within the range of between about 9 and 11 grams; and
   (d) said distilled water being present within the range of between about 85 and 115 milliliters.

3. The device of claim 2, further characterized by said composition further including;
   (a) sodium acetate;
   (b) glutamine; and
   (c) a non-ionic polysorbate surfactant.

4. The device of claim 3, further characterized by
   (a) said sodium acetate being present within the range of between about 4 and 6 grams;
   (b) said glutamine being present within the range of between about 0.15 and 0.25 grams; and
   (c) said surfactant is a one percent solution of polyoxyethylene sorbitan monoleate present within the range of between about 0.5 and 0.7 milliliters.

5. The device of claim 3, further characterized by
   (a) said sodium acetate being present in said composition in an amount effective to provide within the range of between about 0.4 and 0.6 percent of said sodium acetate in a urine sample introduced into said device.

6. The device of claim 3, further characterized by
   (a) said glutamine being present in said composition in an amount effective to provide within the range of between about 0.015 and 0.025 percent of said glutamine in a urine sample introduced into said device.

7. The device of claim 3, further characterized by
   (a) said surfactant being present in said composition in an amount effective to provide within the range of between about 0.0005 and 0.0007 percent of said surfactant in a urine sample introduced into said device.

* * * * *